(12) United States Patent
Chow

(10) Patent No.: US 8,118,803 B1
(45) Date of Patent: Feb. 21, 2012

(54) DEFLECTABLE CATHETER ASSEMBLY

(75) Inventor: Mina Chow, Campbell, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1245 days.

(21) Appl. No.: 11/613,145

(22) Filed: Dec. 19, 2006

(51) Int. Cl.
*A61M 25/00* (2006.01)

(52) U.S. Cl. .................. 604/524; 604/163; 604/164.09; 604/525

(58) Field of Classification Search .................. 600/433, 600/585; 604/95.01, 163, 164.08, 164.09, 604/523
See application file for complete search history.

(56) References Cited

U.S. PATENT DOCUMENTS

| | | | | |
|---|---|---|---|---|
| 5,487,757 A | * | 1/1996 | Truckai et al. ............... 604/264 |
| 5,718,678 A | * | 2/1998 | Fleming, III ................... 604/43 |
| 5,769,812 A | * | 6/1998 | Stevens et al. ............... 604/4.01 |
| 5,876,373 A | | 3/1999 | Giba et al. |
| 5,897,529 A | * | 4/1999 | Ponzi ........................ 604/95.04 |
| 5,921,982 A | | 7/1999 | Lesh et al. |
| 6,004,310 A | * | 12/1999 | Bardsley et al. .............. 604/524 |
| 6,102,926 A | | 8/2000 | Tartaglia et al. |
| 6,120,520 A | | 9/2000 | Saadat et al. |
| 6,126,654 A | | 10/2000 | Giba et al. |
| 6,231,587 B1 | | 5/2001 | Makower |
| 6,251,092 B1 | * | 6/2001 | Qin et al. .................... 604/95.01 |
| 6,251,104 B1 | | 6/2001 | Kesten et al. |
| 7,037,290 B2 | * | 5/2006 | Gardeski et al. ............ 604/95.01 |
| 7,044,934 B2 | * | 5/2006 | Mickley .................... 604/164.01 |
| 2001/0041865 A1 | * | 11/2001 | Delaney et al. ........... 604/102.01 |
| 2002/0032457 A1 | * | 3/2002 | Sirhan et al. ................... 606/195 |
| 2002/0115983 A1 | * | 8/2002 | Sekino et al. .................. 604/528 |
| 2003/0171709 A1 | * | 9/2003 | Constantz et al. ............... 604/22 |
| 2004/0208845 A1 | * | 10/2004 | Michal et al. .............. 424/78.24 |
| 2004/0242527 A1 | * | 12/2004 | Stokes et al. ...................... 514/44 |
| 2004/0263857 A1 | * | 12/2004 | Basavanhally et al. ........ 356/480 |
| 2005/0273006 A1 | * | 12/2005 | Stewart et al. ................. 600/433 |
| 2005/0273145 A1 | * | 12/2005 | Saab .............................. 607/113 |
| 2006/0265036 A1 | * | 11/2006 | O'Connor et al. ............ 607/105 |
| 2006/0282039 A1 | * | 12/2006 | Duong et al. .................. 604/113 |
| 2007/0010782 A1 | * | 1/2007 | Doty et al. ....................... 604/20 |

* cited by examiner

*Primary Examiner* — Nicholas Lucchesi
*Assistant Examiner* — Gerald Landry, II
(74) *Attorney, Agent, or Firm* — Angela Augustus; Blakely, Sokoloff, Taylor & Zafman, LLP

(57) ABSTRACT

A deflectable catheter assembly and methods of use are herein disclosed. The catheter assembly, in one embodiment, is deflectable and includes a first catheter, a second catheter, and a third catheter. The second catheter fits coaxially within the first catheter. In some embodiments, the first and/or second catheter can be constituently different from proximal end to distal end. At least one of the first catheter and the second catheter include a deflectable portion to allow deflection of that catheter from a first position to a second position. The third catheter has a sheath and a medical instrument positioned within the sheath. The third catheter fits coaxially within the second catheter.

24 Claims, 17 Drawing Sheets

DEFLECTABLE CATHETER ASSEMBLY

FIELD OF INVENTION

Deployable medical devices.

BACKGROUND

Systems currently exist that supply therapeutic substances through a medical instrument to regions of a patient's body. Such regions may include a diseased blood vessel, body cavity or organ. In the case of a diseased blood vessel, for example, the therapeutic agent may be used to treat an arterial lesion and/or to promote an angiogenic response.

Medical instruments such as needles and ablation electrodes attached to the distal end of a catheter assembly are used to treat regions within the patient's body. For example, in applying or delivering a therapeutic substance that promotes angiogenesis, a catheter with a needle disposed therein may be guided through the body to the left ventricle of the heart where the needle delivers a therapeutic agent to the left ventricle wall. U.S. Pat. No. 6,120,520, for example, describes a catheter which may be guided through blood vessels in the body to the left ventricle in order to deliver a bioagent into the ventricle's wall. U.S. Pat. Nos. 6,251,104 and 6,102,926 also describe catheters which may be used to guide a treatment device (e.g. a tissue ablation device) through the body and into the left ventricle for treatment of the myocardium.

These types of catheter systems eliminate the need for prior intra-operative procedures, such as a procedure in which the chest cavity is opened to penetrate the heart wall. Intra-operative procedures can subject a patient to prolonged recovery periods and can often lead to further complications. However, there are many difficulties associated with guiding a catheter through the body and introducing the catheter into a particular body cavity or vessel wall. One such difficulty is the maneuverability of the catheter for advancing it through the body while maintaining sufficient strength and rigidity. Often catheters are not shaped adequately for maneuvering through particular portions of the body or to fit a particular body cavity. In addition, catheters are often insufficiently flexible to be maneuvered properly within the particular body cavity.

Another difficulty is maneuvering a medical instrument attached to the catheter to a particular target area in the body cavity. For example, difficulties may arise in positioning the medical instrument within the left ventricular cavity after the distal end of the catheter has extended into the ventricular cavity. The catheter may have sufficient rigidity and strength to be inserted into the body cavity. However, a problem can occur when the catheter is not sufficiently flexible to position the medical instrument to a target site within the body cavity.

SUMMARY OF INVENTION

Embodiments of a catheter assembly and methods of use are disclosed herein. In some embodiments, the catheter assembly includes a first catheter, a second catheter, and a third catheter. The second catheter can fit coaxially within the first catheter. In some embodiments, the first and/or second catheter can be constituently different from proximal end to distal end. At least one of the first catheter and the second catheter can include a deflectable portion to allow deflection of the catheter from a first position to a second position, and the other of the first catheter and second catheter includes a portion which is preshaped (e.g. an angled portion formed by two segments of the angled portion). The third catheter can have a sheath and a medical instrument positioned within the sheath. The third catheter can fit coaxially within the second catheter.

DETAILED DESCRIPTION

Figure 1:
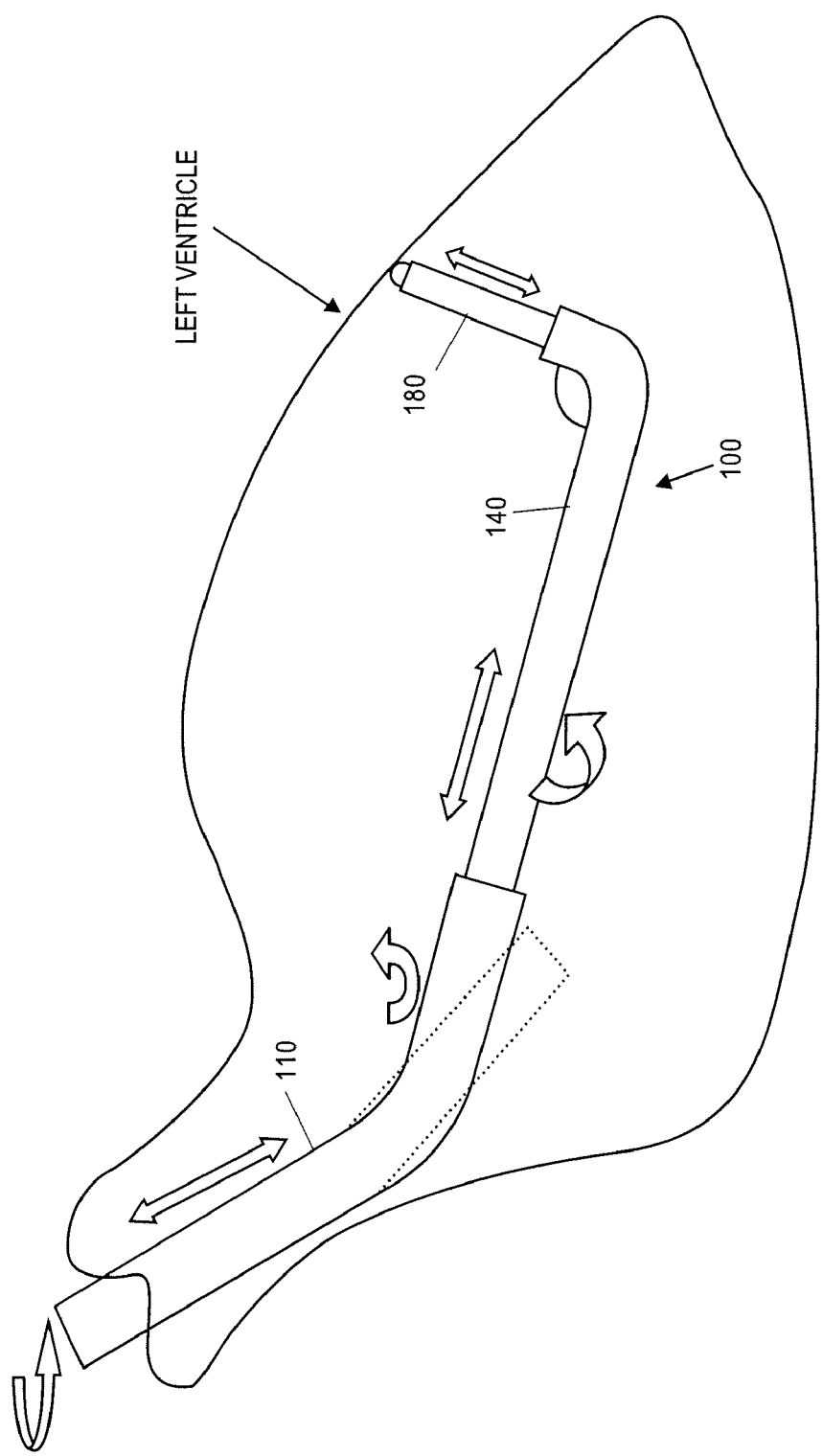
FIG. 1 illustrates a plan view of one embodiment of a catheter assembly disposed within a left ventricle of the heart.

FIG. 1 illustrates a plan view of one embodiment of a catheter assembly disposed within a left ventricle of the heart. Catheter assembly 100 is shown to be extending from the aortic valve into the left ventricle of the heart. Catheter assembly 100 includes a first catheter 110, a second catheter 140, and a third catheter 180. Second catheter 140 can fit coaxially within first catheter 110. Third catheter 180 can fit coaxially within second catheter 140. Each catheter is free to move longitudinally and radially relative to the other catheters. In one embodiment, first catheter 110 may be an outer guide. In one embodiment, third catheter 180 may be a needle catheter which has a lumen therethrough that may accommodate a needle. In another embodiment, third catheter 180 may be adapted to deliver other devices to a treatment site, such as an ablation device.

In some embodiments, catheter assembly 100 may be used for local delivery of bioagents such as, but not limited to, cells used for cell therapy, one or more growth factors used for angiogenesis or arteriogenesis, or vectors containing genes for gene therapy, to the left ventricle. In one embodiment, catheter assembly 100 may be used in delivering cells to treat heart failure or to treat one or more portions of the heart which are ischemic. Catheter assembly 100 uses coaxially telescoping catheters 110, 140, and 180, at least one or more being deflectable, to position a medical instrument at different target sites within a body organ such as the left ventricle. Catheter assembly 100 can be flexible enough to bend according to the contours of the body organ. Catheter assembly 100 is flexible in that catheter assembly 100 may achieve a set angle according to the medical procedure required. Catheter assembly 100 will not only allow some flexibility in angle changes, but can move in a three coordinate system allowing an operator greater control over its movement.

In one embodiment, one catheter in catheter assembly 100 includes a deflectable portion. The deflectable portion allows catheter assembly 100 the flexibility to bend according to the contours in a particular body organ. In one embodiment, the flexible portion is a part of first catheter 110. In an alternative embodiment, the flexible portion is a part of second catheter 140. In other alternative embodiments, both first catheter 110 and second catheter 140 may include deflectable portions.

Also, in certain embodiments, one of first catheter 110 and second catheter 140 includes a shaped portion which is a portion having a fixed, predetermined initial shape from which deflections may occur. For example, second catheter 140 shown in FIG. 1 includes, at its distal portion, a fixed, predetermined initial shape in which a first and second distal portion of second catheter 140 form an initial angle which determines this initial shape. This initial angle may be between about 75 degrees to about 150 degrees. In the example shown in FIG. 1, the distal portion of second catheter 140 has two portions which form a pre-shaped angle of about 90 degrees. The deflectable portion of first catheter 110, in combination with the preshaped portion of second catheter 140, allow for the distal tip of third catheter 180 to be selectively and controllably placed at a multitude of positions. It will be appreciated that the deflectable portion may alternatively be on the second catheter and the preshaped portion may be on the first catheter.

Figure 2A:
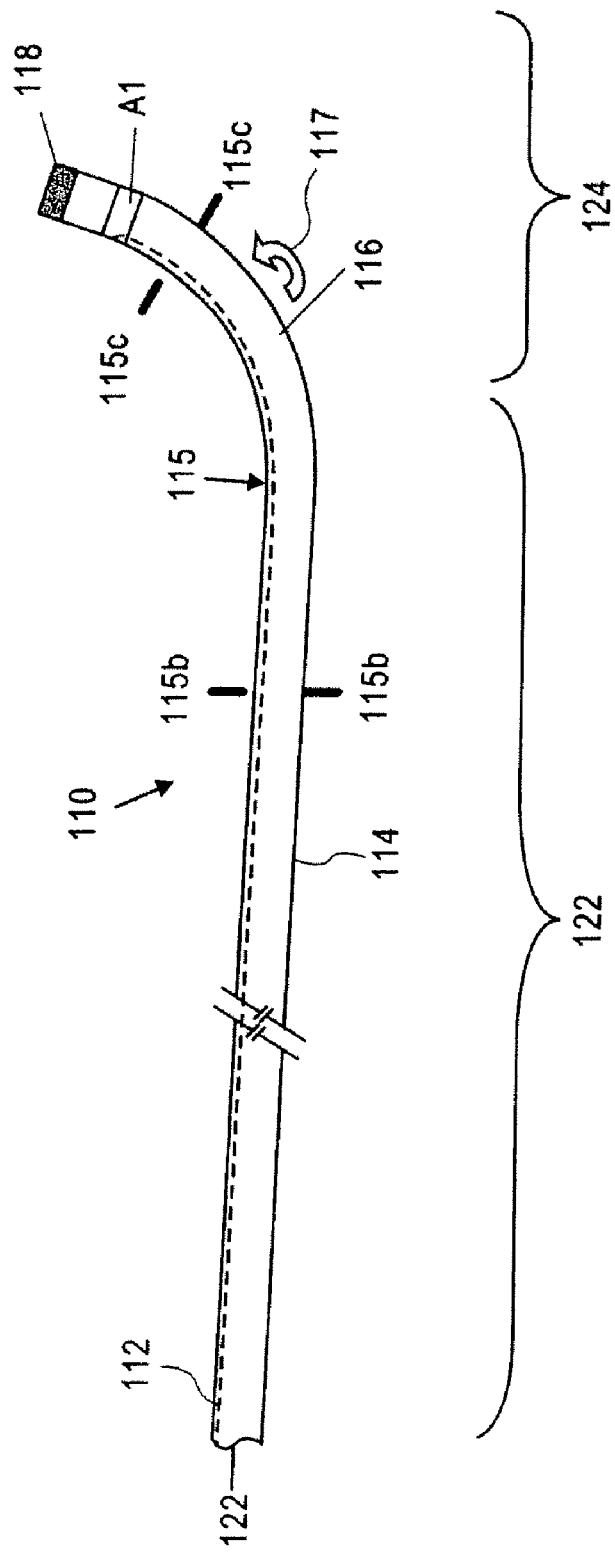
FIG. 2*a* illustrates a sideview of one embodiment of a first catheter of the catheter assembly shown in FIG. 1.

FIG. 2a illustrates a side view of one embodiment of first catheter 110 of FIG. 1. First catheter 110 acts as a guiding catheter. First catheter 110 provides support and orientation direction to the other catheters 140 and 180. In one embodiment, first catheter 110 provides support and orientation to the other catheters 140 and 180 across the aortic valve.

As shown in FIG. 2a, first catheter 110 includes a shaft with a proximal end 122 and a distal end 124. In one embodiment where first catheter 110 includes a deflectable portion, the shaft is made up of a stiff portion 114 and a deflectable portion 116 as shown in FIG. 2a. The difference in stiffness may be achieved by having a wire braid reinforcement along the stiff portion and no wire braid reinforcement along the deflectable portion; other ways to achieve this difference include using different materials in the two portions. The difference in stiffness may range from about 72 D durometer to about 40 D durometer. The distal end portion of the first catheter which is not reinforced (and hence more flexible) may range from about 40 mm to about 120 mm in length. Location 115 shows, in one exemplary embodiment, the transition area between stiffer portion 114 and deflectable portion 116; as noted herein, this transition may be achieved by having a reinforcement layer or material in one portion and not having this layer or material in the other portion. It will be appreciated that both stiffer portion 114 and deflectable portion 116 are normally flexible enough to allow both portions to pass through a patient's vasculature (e.g. from an entry point into the femoral artery to a destination within the left ventricle or within a coronary artery). In an alternative embodiment where first catheter 110 does not include a deflectable portion, the shaft may be made up entirely of stiff portion 114 which resists deflection.

In one embodiment, first catheter 110 may also include a soft distal tip 118 at distal end 124 of the shaft. Soft distal tip 118 can be a soft polymer ring that is mounted at distal end 124 of first catheter 110 to reduce trauma incurred as catheter assembly 100 moves through the body.

In one alternative embodiment, first catheter 110 may be made to have different preshapes. The pre-shapes allow first catheter 110 to enter into specific body cavities and rest in preset positions. For example, once it is delivered into the ventricle, first catheter 110 with a certain preshape rests in the ventricle with preferential positioning. The pre-shape typically includes at least one preset angle between portions of the first catheter; in the example of FIG. 1, the two portions define an obtuse angle.

In one embodiment, the outer diameter of first catheter 110 is approximately 8 French or less. This is the case if second catheter 140, not first catheter 110, includes the deflectable portion. If the deflectable portion is on first catheter 110, then the outer diameter of the second catheter 140 is 6 French. In one embodiment, if the deflectable portion is on second catheter 140, then the outer diameter of the second catheter 140 can be 7 French.

FIG. 2a also illustrates a pull wire 112. Pull wire 112 may be located inside a lumen (e.g. lumen 211 shown in FIG. 2b) of tubing that runs along first catheter 110. Pull wire 112 is attached to an anchor band A1 near the soft distal tip 118. When pull wire 112 is pulled, deflectable portion 116 bends as shown by arrow 117. In one embodiment, the tubing that houses pull wire 112 may be made out of poly[trans-1,2-di (2-furyl)ethylene] (PDFE). In an alternative embodiment the tubing that houses pull wire 112 may be made out of any other flexible polymer. In another alternative embodiment, the tubing that houses the pull wire 112 may be made out of a stacked coil. The wire used for the stacked coil can be any metallic material such as stainless steel, Nitinol, etc. The stacked coil helps to resist compression of the catheter shaft when the pull wire is in tension.

Figure 2B:
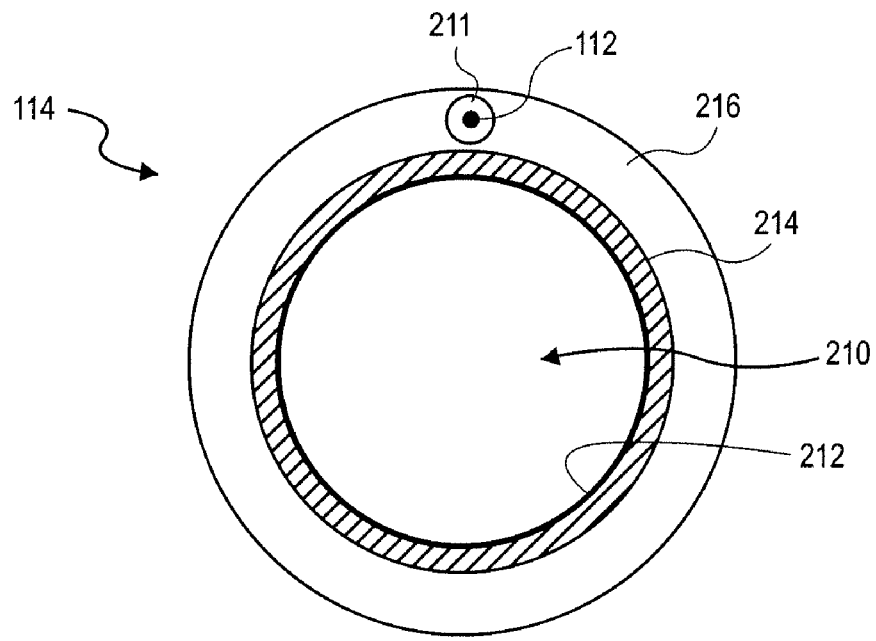
FIG. 2*b* illustrates a cross-section of a stiff portion of the first catheter shown in FIG. 2*a*.
Figure 2C:
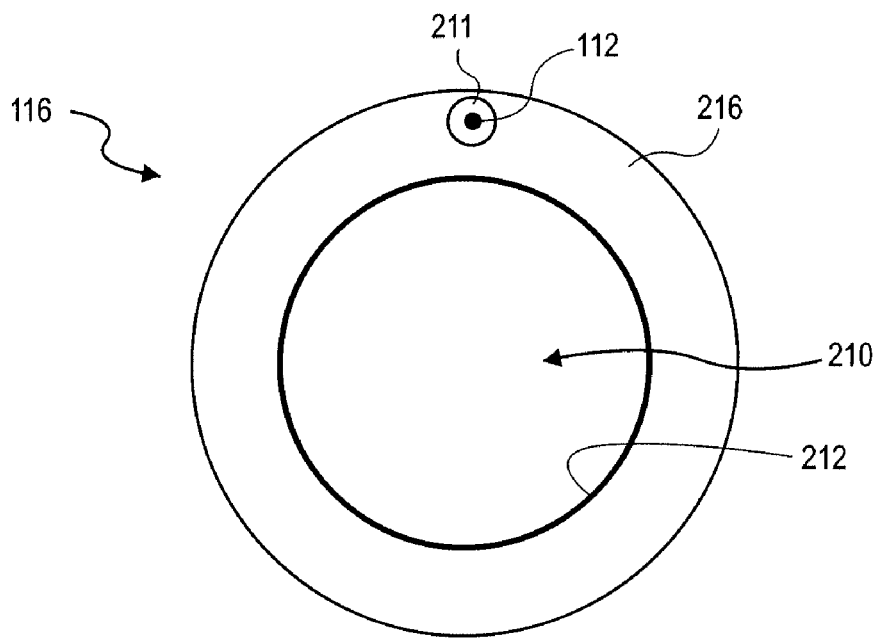
FIG. 2*c* illustrates a cross-section of a flexible portion of the first catheter shown in FIG. 2*a*.

FIG. 2b illustrates a cross-section of stiff portion 114 (taken at location 115b) of first catheter 110 shown in FIG. 2a. As shown in FIG. 2b, the stiff portion 114 of first catheter 110 includes a liner 212, a braided reinforcement 214, and a jacket 216. Jacket 216 includes a lumen 211, formed in jacket 216, and pull wire 112 passes through lumen 211 as shown in FIGS. 2b and 2c. In one embodiment, to build stiff portion 114 of shaft, a mandrel is inserted inside of liner 212 for support. Liner 212 may be made of PTFE (polytetrafluoroethylene) to produce a lubricious inner lumen surface. Interior lumen 210 of liner 212 is designed to hold the second catheter which coaxially fits within this lumen of liner 212. The outer surface of the PTFE liner is chemically etched to promote adhesion with other materials. Next, a reinforcement material 214 is fabricated onto the outside layer of liner 212. In one embodiment, reinforcement material 214 may be braided. Reinforcement material 214 may be one layer or multiple layers. Next, tubing for pull wire 212 is placed on reinforcement material 214. Next, a jacket 216 is attached to the outside of reinforcement material 214. Shrink tubing (not shown) is wrapped around the outside of the jacket 216 and heated. The shrink tubing will shrink down and cause the other materials to be pushed inward in a fusing process. Accordingly, jacket 216 will melt, penetrating the braid 214, if the reinforcement material 214 is a braided structure, and attach to reinforcement material 214 and the liner 212.

FIG. 2c illustrates a cross-section of flexible portion 116 (taken at location 115c) of first catheter 110 shown in FIG. 2a. Flexible portion 116 is similar to stiff portion 114 but does not include reinforcement material 214 of FIG. 2b. Instead, flexible portion 116 includes jacket 216 wrapped around liner 212 with lumen 210. Pull wire 112 within lumen 211 remains in jacket 216. The outer diameter of the cross-section of the portion 116 may be less than the outer diameter of the cross-section shown in FIG. 2b. The absence of the reinforcement material at the distal portion of the first catheter allows this distal portion to be more flexible than a proximal portion of the first catheter. When pull wire 112 is pulled, the distal portion deflects while the stiffer proximal portion does not deflect.

In one embodiment, flexible portion 116 may include a second type of reinforcement material layer (not shown) between liner 212 and jacket 216. The second type of reinforcement material would be substantially less stiff than reinforcement material 214 of stiff portion 114. This second type of reinforcement material may be a metallic multi-ring structure to help maintain the lumen's opening (e.g. lumen 210) when this portion of the catheter is deflected. It is noted that FIGS. 2b and 2c do not show the second and third catheters within the lumen 210.

In the process of making first catheter 110, the mandrel which is inserted into lumen 210 may be made of wire. In an alternative embodiment, the mandrel may be a glass filled polymer. In another alternative embodiment, the mandrel may be made of other materials, such as polymeric materials, such as a mandrel made of PTFE (polytetrafluoroethylene) that can withstand heat (e.g. such that the material does not melt) when heat is applied to the shaft during the fusing process.

In one embodiment, reinforcement material 214 may be made with stainless steel. In an alternative embodiment, reinforcement material 214 may be made with nickel titanium wires. In another alternative embodiment, reinforcement material 214 may be made with nylon wires. In other embodiments (not shown), the reinforcement material may be braided. In other embodiments (not shown), the reinforcement material may be a stacked coil or a metallic multi-ring structure.

In one embodiment, the tubing that houses pull wire 112 may be positioned within liner 212. In an alternative embodiment, the tubing may be placed between reinforcement material 214 and outer jacket 216. In that case, a first layer of reinforcement material 214 may be underneath the tubing with pull wire 112, and a second layer of reinforcement material may be on top of the tubing with pull wire 112. In another embodiment, multiple pull wires, in corresponding lumens in the jacket 216, may be used to control deflection of the first catheter.

Figure 3A:
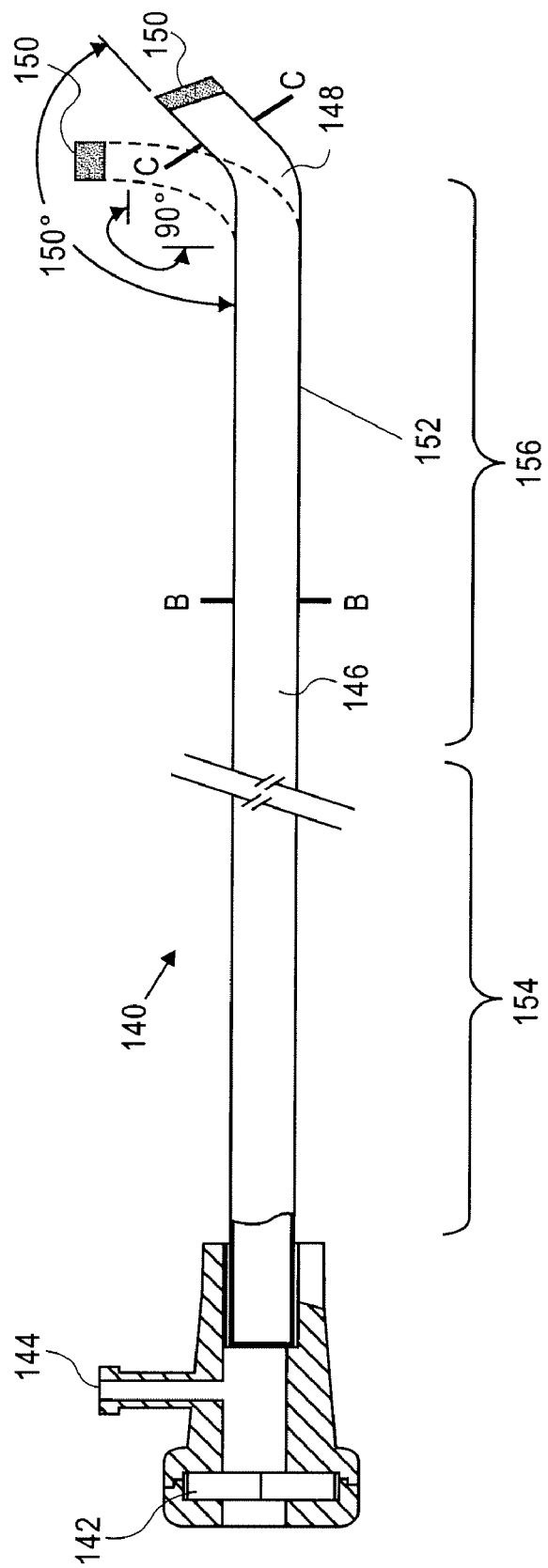
FIG. 3*a* illustrates a sideview of one embodiment of a second catheter of the catheter assembly shown in FIG. 1.

FIG. 3a illustrates a diagram of one embodiment of second catheter 140 of FIG. 1. As discussed above, second catheter 140 may include a flexible portion in one embodiment. In an alternative embodiment, second catheter 140 may not include a flexible portion. In the embodiment shown in FIG. 3a, second catheter 140 includes a shaft 152 having a proximal end 154 and a distal end 156. Shaft 152 includes a stiff portion 146 and a portion 148 which may be a flexible portion or it may have a predetermined initial shape. If portion 148 has a predetermined initial shape, it may also be deflectable from this initial shape. The shaft construction of second catheter 140 is similar to the first catheter 110 but may be made of material with relatively softer durometer ranging approximately from 70 D durometer to 30 D durometer. In one embodiment, shaft 152 also includes a soft distal tip 150 (which is formed from a very low durometer material).

In one embodiment, second catheter 140 may include a flush port 144 and a self-seal valve 142. Self-seal valve 142 ensures that fluid does not flow between second catheter 140 and third catheter 180. Flush port 144 allows flushing of fluid at any time. In an alternative embodiment, first catheter 110 may also include a self-seal valve and a flush port. Flush port 144 may also be used to inject contrast media into the body organ to allow visualization of the body cavity.

In one embodiment, the distal end 156 of second catheter 140 has a predetermined initial shape. This predetermined initial shape is typically an angle formed between two portions of this distal end. Distal end 156 of second catheter 140 may be designed to provide support to third catheter 180 through this predetermined shape. The shape will allow second catheter 140 to direct third catheter 180 to a target (e.g. see FIG. 1). In one embodiment, an angular range for shaped distal end 156 of second catheter 140 is approximately in the range of between 0 degrees to 150 degrees. In the case of FIG. 3a, two exemplary angles of 90 degrees and 150 degrees are shown.

In one embodiment, where portion 148 is deflectable, second catheter 140 is approximately a maximum of 10 centimeters in length longer than the first catheter 110. On second catheter 140, the deflectable portion is no more than approximately 8 centimeters. Third catheter 180 extends less than 8 centimeters from the end of the distal end of second catheter 140. In one embodiment, the third catheter extends 1 or 2 centimeters. The length of third catheter 180 is dependent on the width and length of the heart. It will be appreciated that different sizes may be used, and these different sizes would normally be determined by the size of the organ which is intended to receive the catheter.

Figure 3B:
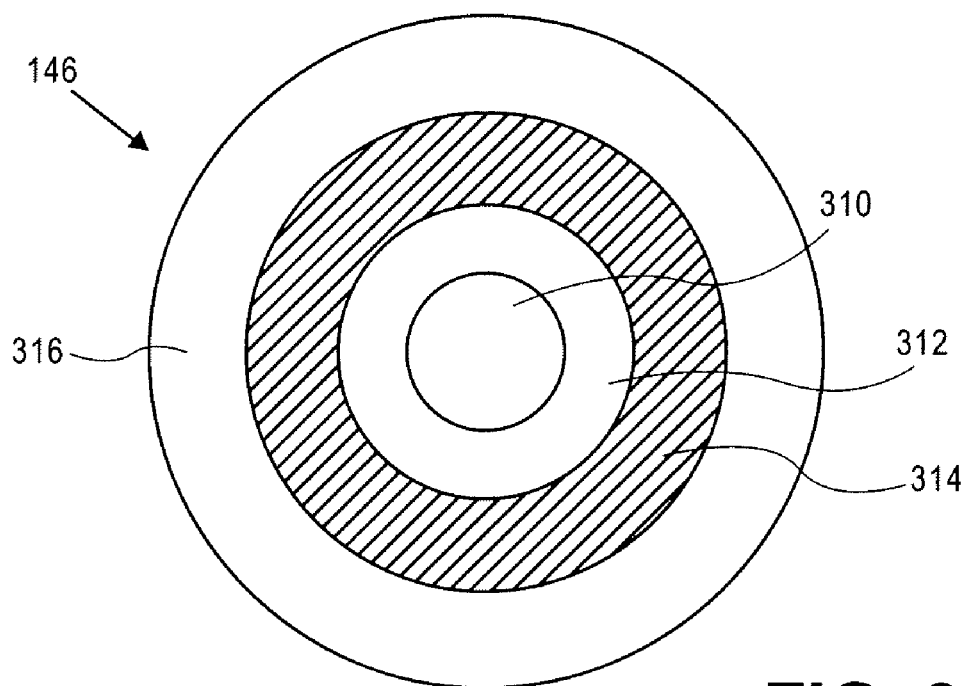
FIG. 3*b* illustrates a cross-section of the stiff portion of the second catheter of FIG. 3*a*.

FIG. 3b illustrates a cross-section of stiff portion 146 of second catheter 140 of FIG. 3a taken at B-B of FIG. 3a. Similar to FIG. 2b, stiff portion 146 includes a liner 312. Liner 312 has a hollow core which is lumen 310 which is designed to coaxially receive the third catheter which is rotatably and slidably moveable within lumen 310. A reinforcement material 314 is fabricated onto liner 312. A jacket 316 circumferentially surrounds reinforcement material 314. In one embodiment, shrink tubing (not shown) is placed around jacket 316. Heat is applied, and the shrink tubing shrinks to cause reinforcement material 314 (e.g. wire braid) to become attached to liner 312. Jacket 316 also then becomes attached to reinforcement material 314. If the reinforcement material is a braided structure, material of jacket 316 may penetrate through reinforcement material 314 and become attached to liner 312.

Figure 3C:
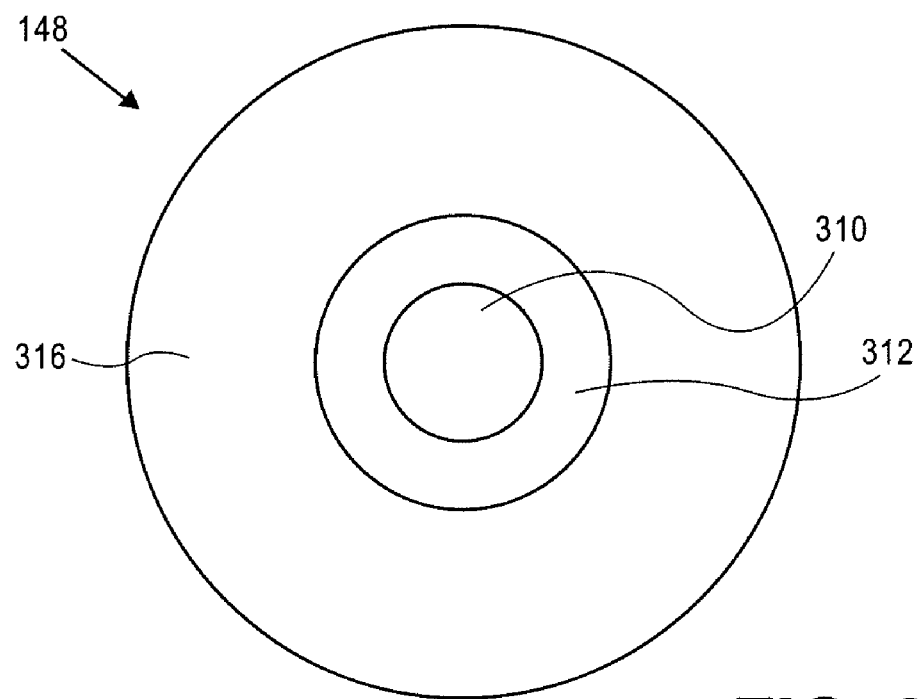
FIG. 3*c* illustrates a cross-section of the deflectable portion of the second catheter of FIG. 3*a*.

FIG. 3c illustrates a cross-section of portion 148 of second catheter 140 of FIG. 3a taken at C-C at FIG. 3a. The cross-section is similar to the cross-section of FIG. 3b except that the portion 148 may not include a reinforcement material 314. Instead, the portion 148 includes a liner 312 and a jacket 316 circumferentially surrounding the liner 312. In alternative embodiments, a second type of reinforcement material (not shown) may be etched or placed between liner 312 and jacket 316 for portion 148. This second type of material may be a metallic multi-ring structure to help maintain the lumen dimension (e.g. the opening of the lumen) when this portion 148 of second catheter 140 is deflected (if it is deflectable).

Figure 4A:
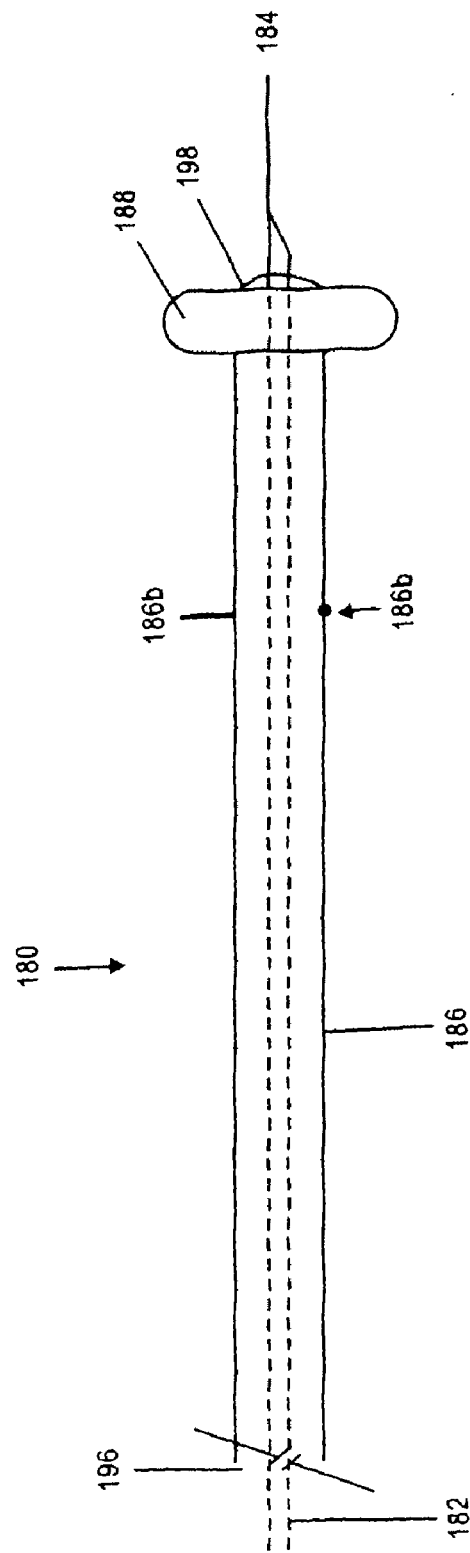
FIG. 4*a* illustrates a sideview of a third catheter of the catheter assembly shown in FIG. 1.

FIG. 4*a* illustrates a side view of a portion of an embodiment of third catheter 180 in FIG. 1. Third catheter 180 guides a medical instrument, such as a needle, to a target area. In one embodiment, third catheter 180 may be a needle catheter as shown in FIG. 4*a*. Third catheter 180 includes a needle sheath 186 housing a needle 182. Needle is 182 moveable longitudinally through sheath 186, and the lumen of the needle extends from a proximal end of needle to the needle tip 184. Needle sheath 186 has a proximal end 196 and a distal end 198. A needle tip 184 of the needle 182 is extendable from distal end 198 of needle sheath 186 (as shown in FIG. 4*a*). While needle 182 is shown as a straight needle with a sharp tip, other types of needles, such as helical (e.g. corkscrew-like) needles may also be used in certain embodiments.

In one embodiment, the outer diameter of needle sheath 186 is between 40 to 60 thousandths of an inch. In one embodiment needle 182 is a 25 to 27-gauge needle. This may be the case if the outer diameter of first catheter 110 is approximately 8 French. The outer diameter may change if the diameter of first catheter 110 increases.

In one embodiment, third catheter 180 may include one or more stabilizers. As seen in FIG. 4*a*, the stabilizer in one embodiment is a balloon 188. Balloon 188 is located near distal end 198 of needle sheath 186. Balloon 188, in this case a tire tube shaped balloon, allows third catheter 180 to approach the target with needle 182 perpendicular to the target. That is, the tire tube shaped balloon will tend to prevent a needle injection at an angle other than approximately 90 degrees into the target tissue. In addition, balloon 188 allows for a larger surface area of control so needle tip 184 or needle 182 does not wobble. For example, as third catheter 180 approaches a wall of the left ventricle, balloon 188 is positioned against the wall of the left ventricle. Needle 182 then extends from sheath 186 and penetrates in some embodiments, the left ventricle wall. Balloon 188 thereby allows for a larger surface area of control against the left ventricle wall to stabilize the needle 182 and hold needle 182 perpendicular to left ventricle wall as it penetrates through the surface of the wall. FIG. 4*f* shows a front perspective view of the needle and balloon of FIG. 4*a*. FIG. 4*g* shows a front perspective view of another embodiment of the third catheter in which a set of balloons 188A, B and C (e.g. three balloons, each coupled to one of the lumens) acts as a stabilizer which is coupled near a distal end of third catheter 180.

Figure 4B:
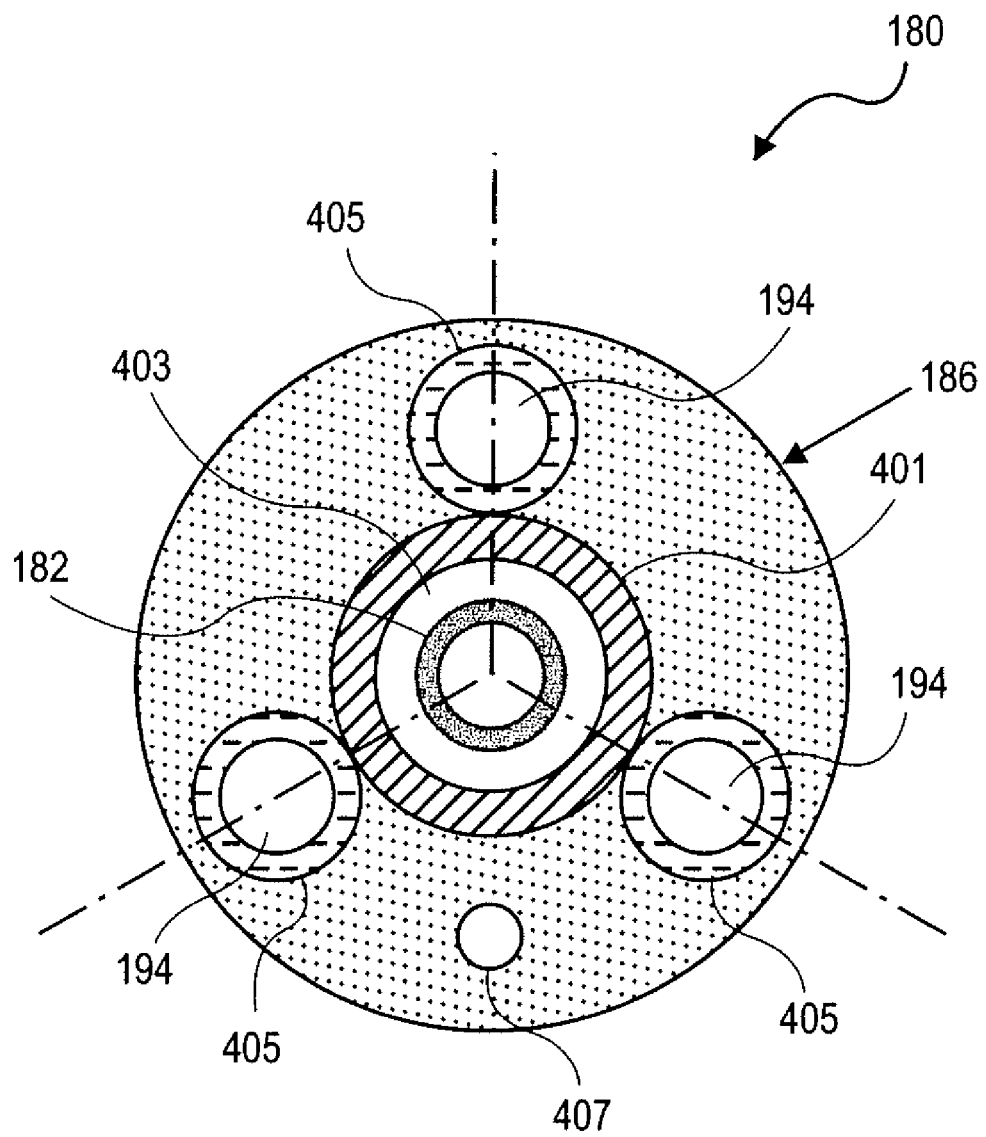
FIG. 4*b* illustrates a cross-section of the third catheter of FIG. 4*a*.
Figure 4C:
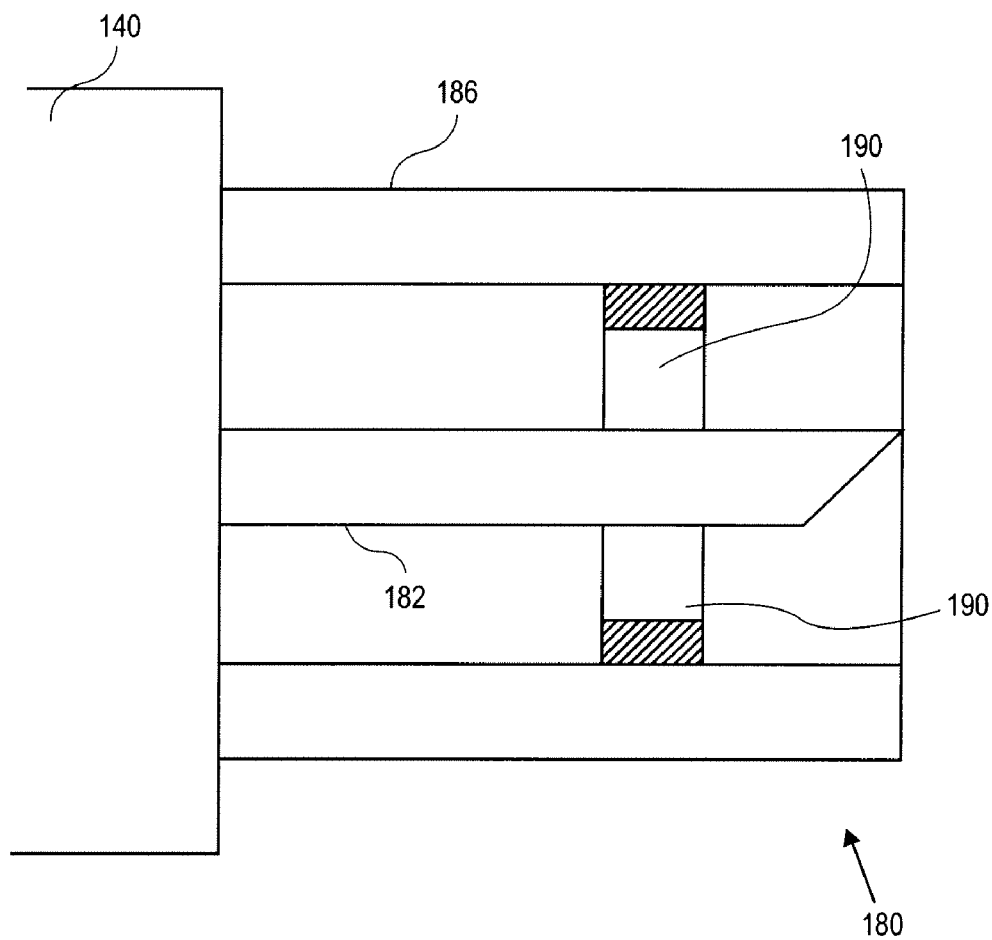
FIG. 4*c* illustrates a cross-section of an embodiment of a needle with a needle stop for use with the third catheter.

FIG. 4*b* illustrates a cross-section (taken at point 186B) of third catheter 180 of FIG. 4*a*. In one embodiment, and as shown in FIG. 4*b*, three balloon lumens 194 are placed between needle 182 and the outer layer of sheath 186. Each balloon, such as balloon 188 (e.g., see FIG. 4*g*), may use a separate balloon lumen 194. In one embodiment, one balloon lumen 194 may used with one balloon stabilizer. In alternative embodiments, additional balloon lumens 194 may be used for only one balloon stabilizer or for more than one balloon stabilizer. In FIG. 4*b*, the three balloon lumens 194 are positioned relative to sheath 186 at various points to provide additional strength to the structure of third catheter 180. This additional strength allows for additional stabilization and prevents buckling of third catheter 180. In one particular embodiment, shown in FIG. 4*b*, three balloon lumens 194 are coupled to a single tire tube shaped balloon 188 (not shown) which is attached to the distal end of third catheter 180 as shown in FIG. 4*a*. These three balloon lumens 194, when inflated, tend to give additional strength to the third catheter. These three balloon lumens 194 are arranged substantially equidistant in relative to the outer circumference of sheath 186 in order to provide a substantially equal distribution of support to the third catheter; in particular, they are separated by about 120 degrees. These lumens 194 are created by tubular liners 405 which are embedded, in one embodiment, into sheath 186. Another tubular liner 401 forms lumen 403 which slidably receives needle 182. Lumen 403 extends from the distal end of third catheter 180 to the proximal end of third catheter 180. Lumens 194 extend from proximal end 196 to distal end 198. At or near distal end 198, lumens 194 can be in fluid communication with balloon(s) 188. At or near proximal end 196, lumens 194 can be in fluid communication with a source for an inflation fluid which is used to inflate balloon(s) 188. Lumen 407 is an optional lumen for use with a pull wire (not shown) which may be used to deflect third catheter 180 in certain embodiments.

Figure 4D:
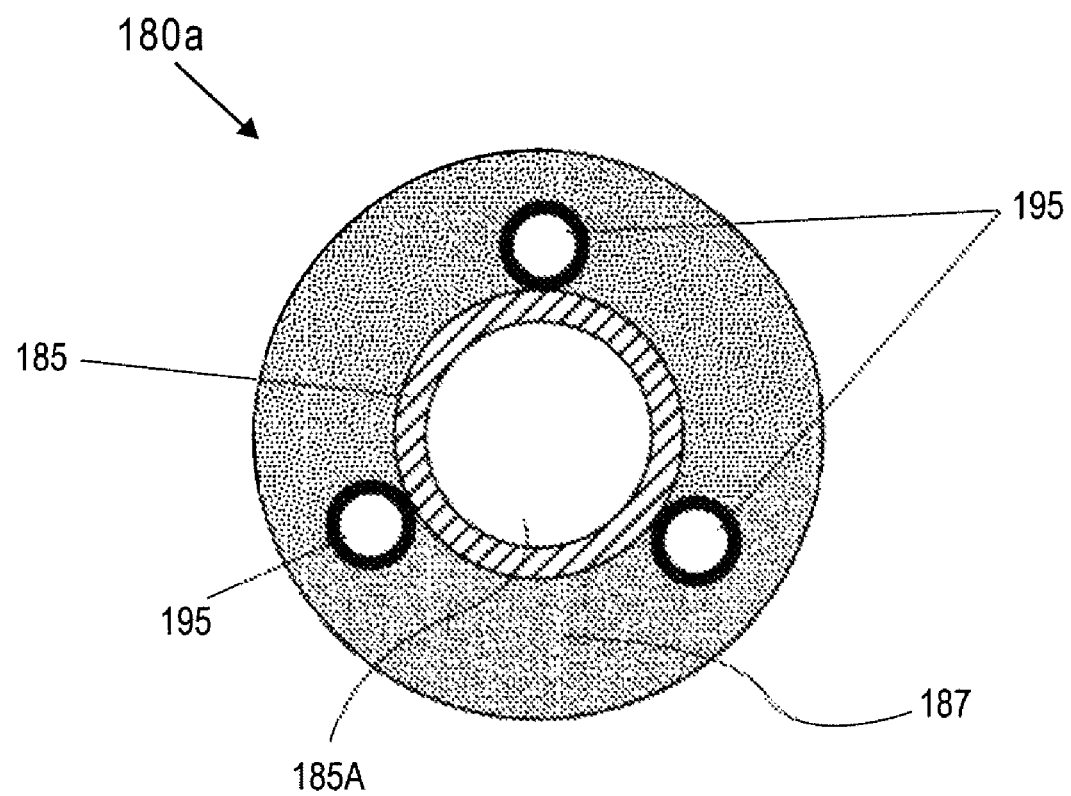
FIG. 4*d* shows a cross-sectional view of an alternative embodiment third catheter.

FIG. 4*d* illustrates a cross-section of an alternative embodiment of third catheter 180 of FIG. 4*a*. In one embodiment, third catheter 180 is made of a liner 185 which surrounds a lumen 185A, a jacket 187 and peripheral lumens 195. In one embodiment, liner 185 is made of a lubricious polymer such as PTFE or HDPE (High Density Polyethylene). Liner 185 may also be structured similar to the first and second catheters in that it has a lubricious sub-liner, reinforced on the outside by a braid or coil structure, and surrounded by a jacket material that all are fabricated using the heat process described for the first and second catheters. The jacket material may be polyimide such that it is coated on, instead of heat fused on, liner 185. This kind of structure gives the stiffness needed for small third catheter 180. Peripheral lumens 195 may be constructed in several ways. In one way, it may be constructed by bonding polyimide tubes in between liner 185 and jacket 187. This offers additional rigidity to third catheter 180. It may also be formed by placing processing mandrels in between jacket 187 and liner 185 during the heat fuse process. The mandrels are removed after the process and lumens 195 are formed. Lumen 185A is a channel through which a medical instrument, such as needle 182, slidably extends.

In certain embodiments, the shape of the balloon 188 may vary. It should be noted that the balloon 188 should collapse back, when not inflated, to the original shaft size of third catheter 180. Therefore, balloon 188 is generally made of elastomer materials.

FIG. 4*c* illustrates a cross-section of an alternative embodiment of a needle 182 with a needle stop 190. Needle sheath 186 is shown extending from second catheter 140. Needle sheath 186 houses needle 182. In FIG. 4*c*, needle 182 includes one or more needle stops 190. Needle stops 190 allow needle 182 to extend from the distal end of needle sheath 186 and penetrate tissue to a predetermined depth. Needle 182 extends from needle sheath 186 and begins penetrating body tissue. As needle 182 is extended, needle stops 190 also contacts the tissue preventing needle 182 from extending further into the tissue. Accordingly, needle 182 is automatically stopped from extending further into body tissue when needle stop 190 contacts the body tissue. Needle stops 190 may be placed a predetermined distance from the tip of needle 182 so that needle 182 only penetrates the tissue a predetermined amount. Needle stop 190 effectively removes control of the penetration depth of the needle from the operator and therefore reduces operator error.

In one embodiment of the arrangement shown in FIG. 4*c*, needle stop 190 may be a ring around needle 182. The ring may be glued onto needle 182. In an alternative embodiment, the ring may be a melted polymer around needle 182. In another alternative embodiment, the ring may be encased in platinum or gold for purposes of visibility. It should be noted that needle stop 190 could be soldered onto needle 182 as well. In one embodiment, needle stop 190 may be made of nickel titanium, which has to be glued rather than soldered to needle 182.

Figure 4E:
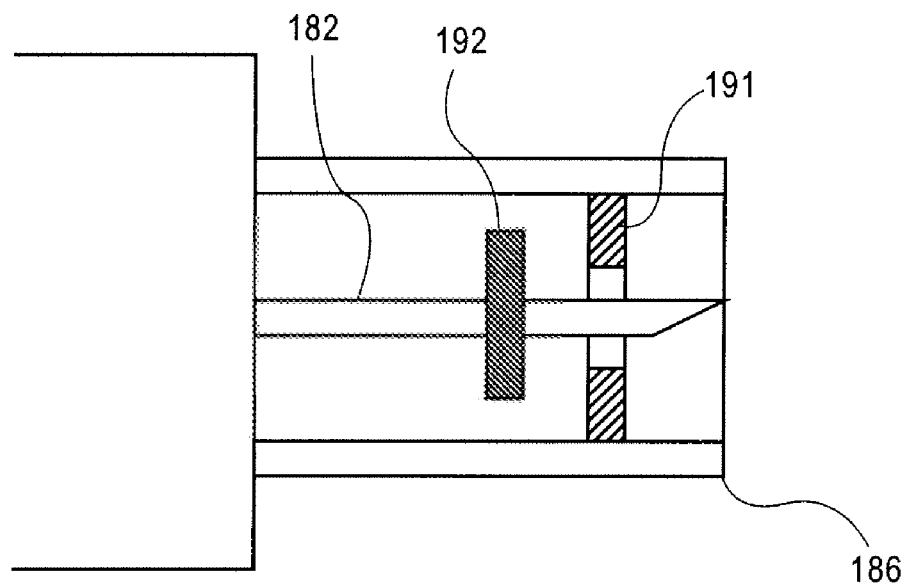
FIG. 4*e* illustrates a cross-section of an alternative embodiment of a needle stop for the third catheter of FIG. 4*a*.
Figure 4F:
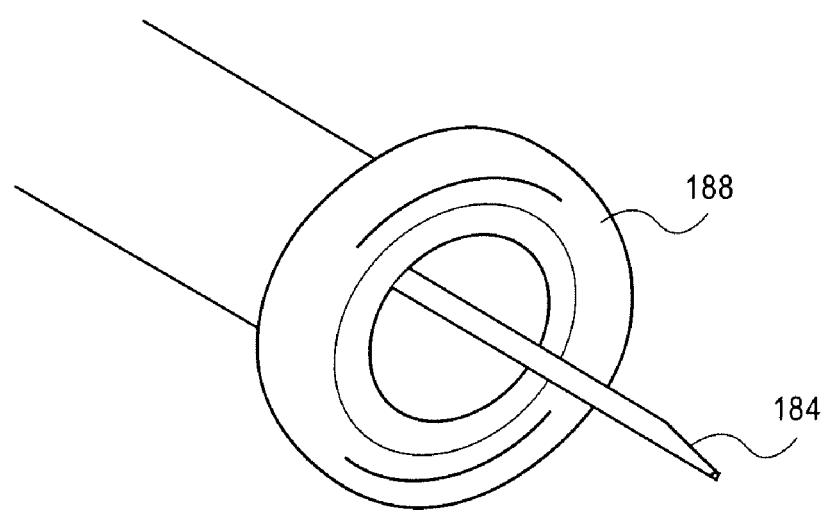
FIG. 4*f* shows a front perspective view of a needle and a balloon of the third catheter shown in FIG. 4*a*.
Figure 4G:
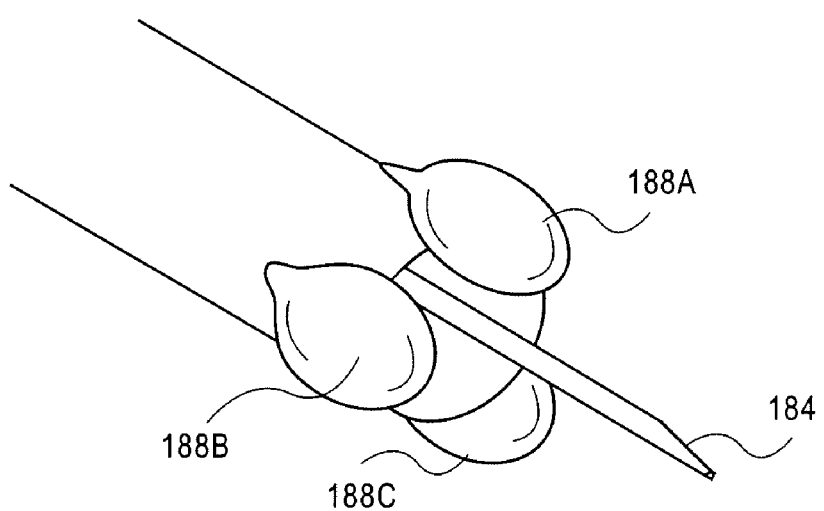
FIG. 4*g* shows a front perspective view of a needle and a set of balloons for a third catheter.

FIG. 4e illustrates a cross-section of an alternative embodiment of a needle stop arrangement which includes a needle stop 192 attached to the distal end of needle 182. In this embodiment, a ring 191 is assembled on the inner surface of needle sheath 186. Ring 191 is fixedly attached to this inner surface and has an opening which allows the distal end of the needle to pass beyond the ring and beyond the end of sheath 186. The stop 192 on the needle will not pass through the opening in ring 191. When the needle 182 is extended forward to penetrate the tissue to a pre-determined distance, needle stop 192 on the needle engages the ring 191 on needle sheath 186, and causes the needle to stop extending, thereby limiting the penetration of the needle. Stop 192 and ring 191 function to limit the penetration of the needle (thereby preventing the needle from making a puncture completely through the wall of the left ventricle, for example) and to also set a predetermined penetration depth (based on the placement of stop 192 on the needle relative to the needle's length beyond the stop 192 and the position of ring 191 in the sheath).

In those embodiments which use at least one needle, the needle may be a hollow tube with a beveled distal tip and a proximal hub attachment with an injection port. The needle may be made of a metallic material such as stainless steel, nickel titanium, platinum, etc. The needle will typically have enough flexibility to be pushed through a patient's vasculature and still not buckle when the distal tip is pushed into penetration with the patient's tissue (e.g. into the myocardium within the left ventricle).

In one embodiment, third catheter 180 includes a proximal hub with an injection port. The injection port is connected to the needle lumen to allow fluid communication from the injection port to the needle lumen, thereby allowing the introduction of a bioagent from the injection port and into the needle lumen and then into the tissue penetrated by the distal tip of the needle. The proximal hub with the injection port may include a luer lock. In another embodiment third catheter 180 may also include a self-seal valve and a flush port. The medical instrument, such as the needle, runs inside of the self-seal valve.

Figure 5:
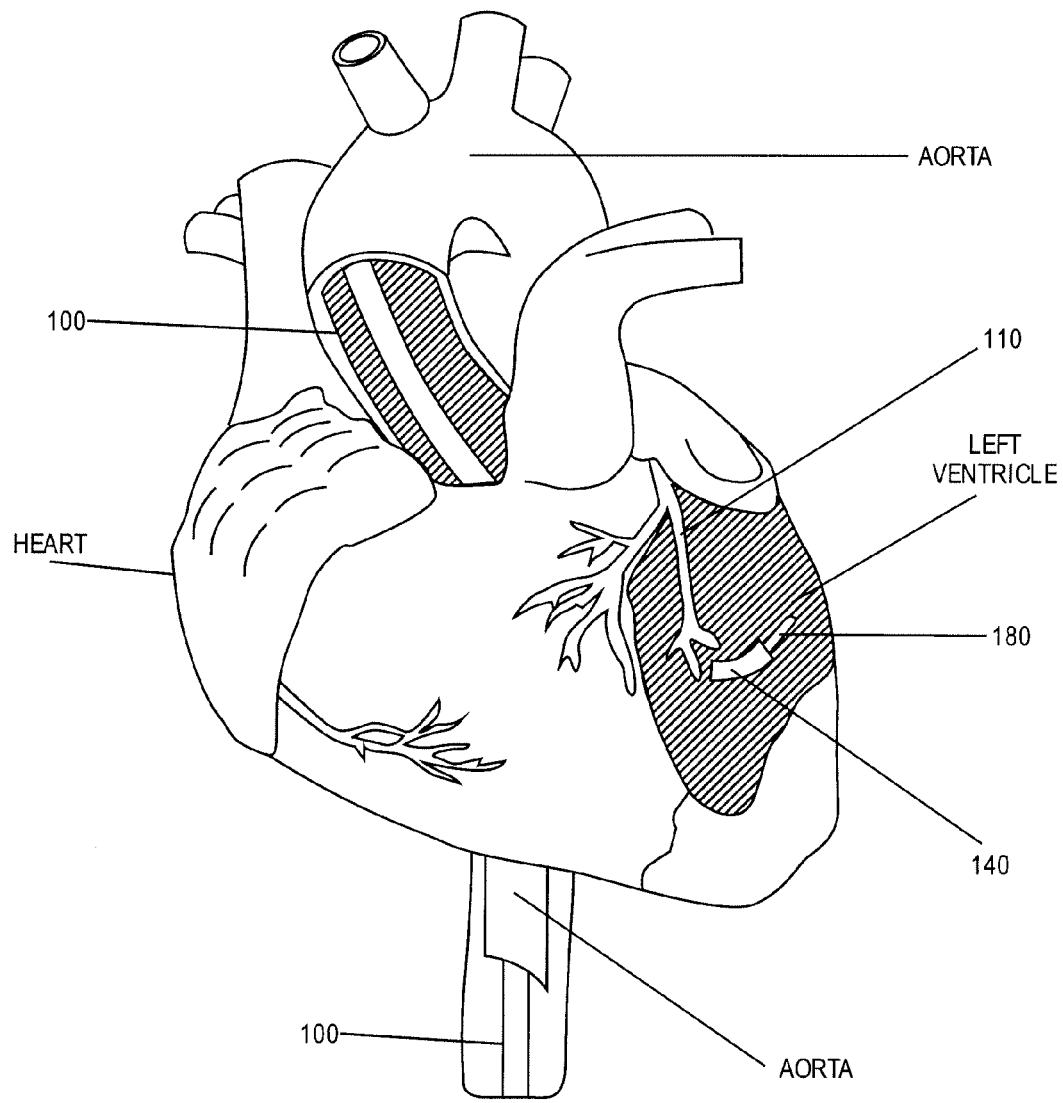
FIG. 5 illustrates a cross-section of a heart with the aorta and ventricle open partially to demonstrate use of a catheter assembly.

FIG. 5 illustrates a cross-section of a heart with the aorta and ventricle open partially to demonstrate the use of catheter assembly 100. Catheter assembly 100 accesses the ventricle through the aorta. A guide wire (not shown) and an introducer sheath (not shown) are first introduced into the femoral artery from the groin area (not shown); other entry sites may alternatively be used. The guide wire is then tracked through the aorta across the aorta valve. Then, first catheter 110 is inserted through the introducer sheath and is tracked over the guide wire into the left ventricle. The distal end of first catheter 110 is deflected so that the first catheter's distal tip is pointed in a direction approximately parallel to the wall of the target injection site. The guide wire is then removed from the vessel.

Second catheter 140 and third catheter 180 are introduced into the inside of first catheter 110 and into the left ventricle. Once first catheter 110 enters the left ventricle from the aortic valve, first catheter 110 may be deflected to position second and third catheters 140 and 180 towards the target wall. The deflection may be achieved by pulling wire 112 in lumen 211 in the case of the first catheter 110 shown in FIG. 2a. Second catheter 140 is extended to bring third catheter 180 close to the wall. Extension and rotation of the second catheter 140 positions a medical instrument such as a needle along the length and radial wall of the left ventricle. In one embodiment, one or more electrodes may be positioned in one or more of the catheters to sense wall contact or to sense electrophysiological activity of the heart's wall or to sense oxygen levels or other parameters in the myocardium.

With support from second catheter 140, third catheter 180 extends out a small distance to reach the wall. The needle then extends out a fixed length to puncture into the myocardium to deliver a bioagent. In one embodiment, a medical instrument such as a laser compatible optical fiber may be used in place of the needle. In alternative embodiments other medical instruments, such as laser ablater or RF ablater or a sensor (such as a sensor to detect eletrophysiological activity or oxygen content in the myocardium) may be used with catheter assembly 100 in place of the needle. In other embodiments, the third catheter includes a needle and another medical instrument such as an electrophysiological sensor or an oxygen sensor. In yet other embodiments, the third catheter includes a medical instrument and a transducer coil or other transducer which is used to determine the position of the catheter by, for example, measuring the magnetic field received by a transducer coil which is positioned near the distal end of the third catheter.

In one embodiment, catheter assembly 100 may be delivered into the left ventricle without use of a guide wire. In this case, first catheter 110 is first introduced into the aorta through the introducer sheath (not shown). Right before crossing the aortic valve, the distal end of first catheter 110 is pulled to curl back to form a tight loop. Then first catheter 110 is advanced through the aortic valve. The looped distal end prevents injury of the aortic valve due to the movement of first catheter 110.

In one embodiment, catheter assembly 100 may be made to be magnetic resonance imaging (MRI) compatible. To do so, the material selection for all components have to be such that it does not cause artifacts in a MR imaging procedure. To achieve this, the materials should be made with non-magnetizable materials. The braid wire can be either NiTi or Nylon instead of stainless steel. The needle can be NiTi or polymer such as reinforced Polyimide or PEEK. The reinforcement material for the needle can be NiTi or Nylon, instead of stainless steel. The basic design for catheter assembly 100 can remain the same. There may be adjustment of material stiffness needed to achieve the same overall properties of the catheter assembly. This may be done by replacing polymeric material with higher durometer grades to increase the stiffness sacrificed by, for example, replacing the stainless steel with the elastic NiTi in the braid.

Figure 6:
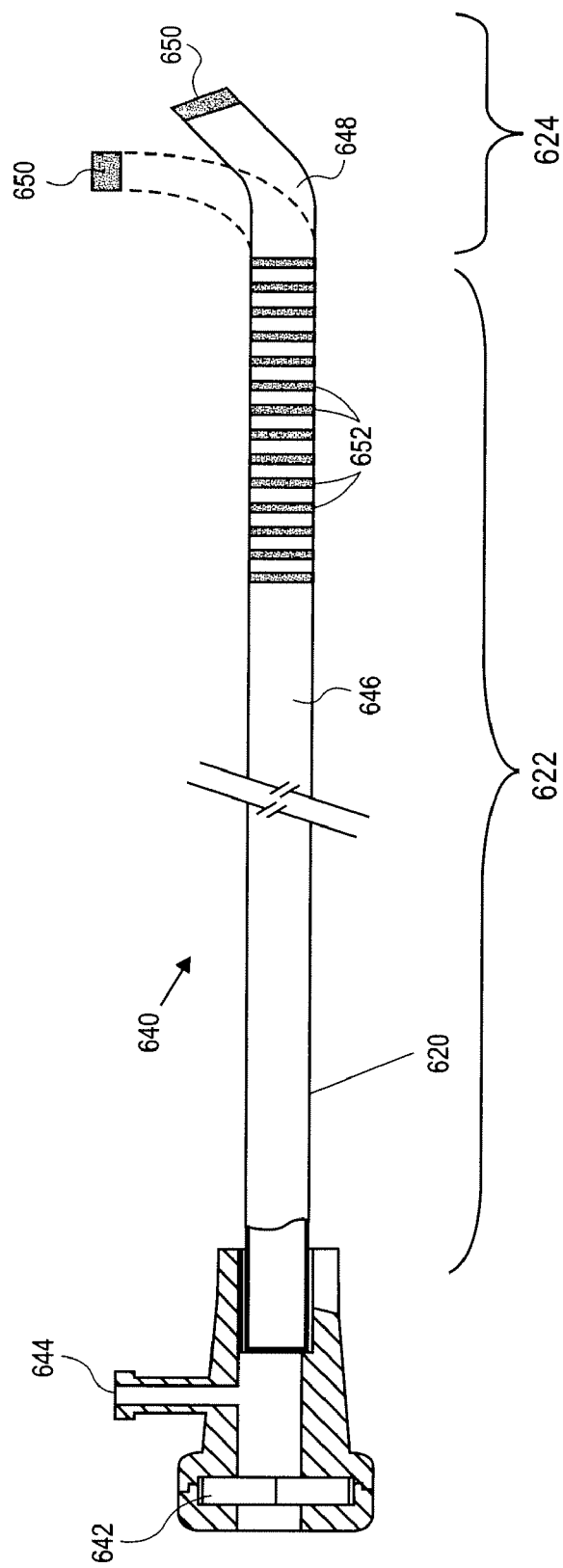
FIG. 6 is a side view of an alternative embodiment of a second catheter.

FIG. 6 illustrates an alternative embodiment of a second catheter 640. Second catheter 640 includes a shaft 620 having a proximal end 622 and a distal end 624. Shaft 620 includes a stiff portion 646 and a flexible portion 648. In one embodiment, second catheter 640 also includes a soft distal tip 650. The soft distal tip 650 may be similar to the one shown in FIG. 2a. In FIG. 6, second catheter 640 is also shown to have radiopaque markers 652. The radio opaque markers 652 may be spaced evenly at a distance ranged approximately between 5 millimeters to about 1 centimeter apart. However, in alternative embodiments, radiopaque markers 652 may be spaced unevenly and at different distances. In addition, in another alternative embodiment, radiopaque markers 652 may be fabricated on the entire second catheter 640. This marker system is used as a ruler. Often the therapy has to be delivered to multiple locations. Opaque markers 652 act as a ruler to help keep track of delivery locations by displaying the extension distance of second catheter 640 relative to the first catheter. In one embodiment, similar to what is shown in FIG. 2a, the second catheter 640 of FIG. 6 includes a flush port 644 and a self-seal valve 642.

Figure 7:
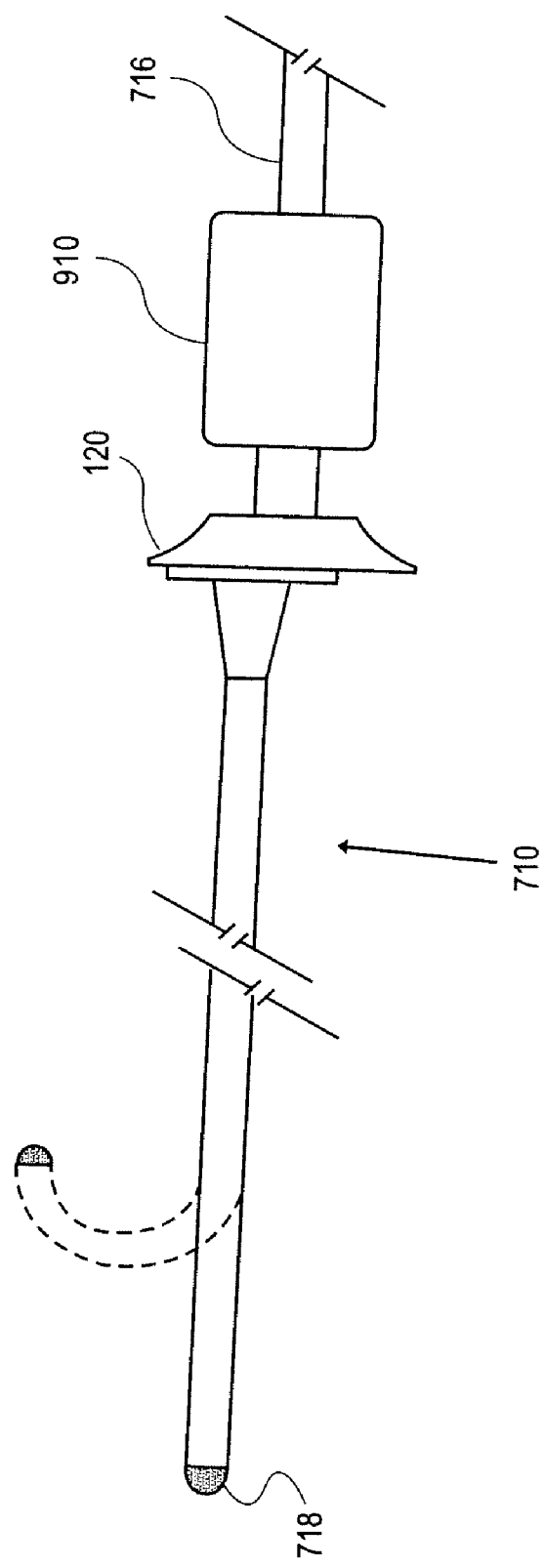
FIG. 7 is a side view of an alternative embodiment of a first catheter with a control handle for deflection of the first catheter.

FIG. 7 illustrates an alternative embodiment of a first catheter 710 with a control handle for deflection of first catheter 710. The control handle comprises a control knob 120 and a handle body 910. A pull wire or tendon wire (not shown) is attached to an inner component that is moveable by a control knob 120 shown on the outside of first catheter 710. In one embodiment, by pulling control knob 120 towards a proximal end 716, first catheter 710 is under tension and is therefore deflected at a distal end 718. To straighten out first catheter 710, control knob 120 is pushed forward. A similar control handle may be used on the second catheter if it is desired to make the second catheter deflectable. In another embodiment, proximal end 716 is internally attached to control knob 120. The tendon wire is internally attached to body 910 of the control handle. By pulling body 910 of the control handle away form control knob 120 towards a proximal end 716, first catheter 710 is under tension and is therefore deflected at a distal end 718. To straighten out first catheter 710, control knob 120 is pulled near handle body 910.

Figure 8A:
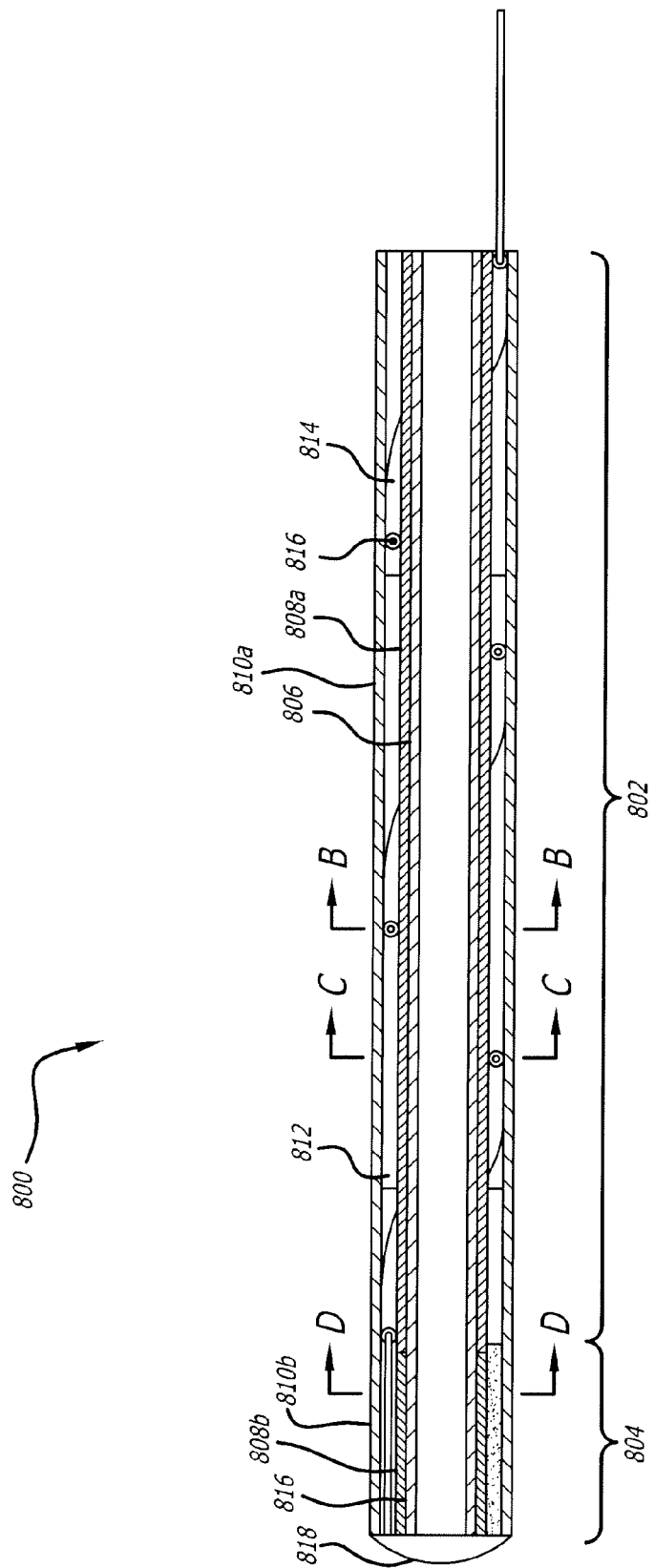
FIG. 8*a* is a side view cross-section of an embodiment of a catheter assembly.

FIG. 8a illustrates a side view cross-section of a catheter assembly according to embodiments of the present invention. Catheter 800 includes proximal section 802 and distal section 804. Catheter 800 can be an assembly of tubular structures housed within each other and generally forming a tube-like construction overall. In some embodiments, both proximal section 802 and distal section 804 of catheter 800 include at least three tubular structures interdisposed within each other. The lumen of proximal section 802 is in fluid communication with the lumen of distal section 804; however, the materials used to construct proximal end 802 and distal end 804 may differ in certain material characteristics. In some embodiments, the materials may be the same.

In one embodiment, catheter 800 can include inner shaft 806 which can extend the length of proximal section 802 and distal section 804. Inner shaft 806 can be made of a polymer with lubricious luminal surface characteristics which can allow for ease of movement for a therapeutic tool. Inner shaft 806 can have a durometer of between 45 D and 72 D. In some embodiments, inner shaft 806 can be made of a low friction material such as HDPE or ePTFE.

Examples of therapeutic tools that can be used in conjunction with inner shaft 806 include, but are not limited to, a needle, a biopsy clamp and a catheter with ultrasonic transducers. Alternative embodiments include a laser compatible optical fiber, a laser ablater or RF ablater or a sensor (such as a sensor to detect eletrophysiological activity or oxygen content in the myocardium). In other embodiments, a combination of a needle and another medical instrument such as an electrophysiological sensor or an oxygen sensor can be used in conjunction with inner shaft 806. In yet other embodiments, a medical instrument and a transducer coil or other transducer which is used to determine the position of the catheter by, for example, measuring the magnetic field received by a transducer coil which is positioned near the distal end of catheter 800 can be used in conjunction with inner shaft 806.

In embodiments in which a needle is the therapeutic tool, bioagents such as stem cells, growth factors, gene, and vectors can be locally delivered to the treatment site. In addition, proteins, peptides and synthetic pharmaceuticals, such as an anti-inflammatory or immune modulating, anti-migratory, anti-thrombotic or other pro-healing agents or a combination thereof. The type of treatment agent delivered to the treatment site is virtually unlimited.

Referring to proximal section 802 in FIG. 8a, catheter 800 can include middle shaft 808a housing inner shaft 806. That is, the luminal surface of middle shaft 808a can be completely or substantially in contact with the abluminal surface of inner shaft 806 in proximal section 802. In one embodiment, middle shaft 808a is a coiled shaft and inner shaft 806 is fitted tightly therein. In one embodiment, middle shaft 808a can be made of multiple layers of stacked coiled tubular structures with each coiled tubular structure winding towards the opposite direction from the coiled tubular structure under or above, respectively. In one embodiment, middle shaft 808a includes three stacked coil tubular structures. To form a coiled tubular structure, in some embodiments, a wire can be wound on a mandrel such that there are no gaps in between adjacent coils forming a coiled tubular structure. The wire may be, for example, stainless steel, NiTi or nylon. The multiple layers of middle shaft 808a can form an inter-locking shaft structure that transmits torque efficiently in either rotational directions of catheter 800 when deployed during a medical procedure.

Outer shaft 810, which includes outer shaft sections 810a and 810b, can serve as the outer housing for catheter 800. Outer shaft 810 can encompass middle shaft 808, i.e., both sections 810a and 810b. Relative to outer section 810b, outer section 810a can be stiffer. Outer shaft section 810a, which is located within proximal section 802, can be made of a material such as Pebax® or Nylon. Outer shaft section 810b, which is located within distal section 804, can be made of a material which is more flexible than the materials of outer section 810a. For example, materials of outer shaft 810b can include, but is not limited to, Pebax®, polyurethane, and polyethylene. In one embodiment, one or more electrodes may be positioned on the circumference of outer shaft 810 to sense wall contact or to sense electrophysiological activity of the heart's wall or to sense oxygen levels or other parameters in the myocardium.

In some embodiments, tendon sheath 814 housing tendon wire 816 can reside between the abluminal surface of middle shaft 808a and the luminal surface of outer shaft 810a. In one embodiment, a gap 812 remains in a portion of proximal section 802 between the abluminal surface of middle shaft 808a and the luminal surface of outer shaft 810a. In other words, gap 812 does not reside the length of proximal section 802, but instead only an intermediate portion thereof. In one embodiment, tendon sheath 814 wraps around middle shaft 808a and is "free-floating" within gap 812. That is, tendon sheath 814 should preferably wrap around middle shaft 808a loosely rather than tautly in gap 812. For applications in which catheter 800 is utilized in curved anatomical lumens, the wrapping of tendon sheath 814 may ensure balancing of the materials over a cross-section of proximal section 802 over a shaft section lying within a curved anatomical location such as the aortic arch. The aortic arch is a curved segment of the aorta that the catheter, if used to target a therapy in the left ventricle accessing the body from the femoral artery, must pass by. Other curved anatomical locations can be the turn from superior vena cava into the right atrium and the turn from right atrium into the coronary sinus, for example. The pitch of the wrap is dictated by the estimated length of a curved anatomical path. "Pitch" refers to the number of wraps with a given length of the catheter shaft. The pitch increases if the number of wraps decreases within the given length of the catheter shaft. In some embodiments, tendon sheath 814 is wrapped around middle shaft 808a for at least one pitch within gap 812. The "free-floating and wrapping" characteristic of a portion of tendon sheath 814 may reduce stored torque and/or eliminate preferred orientation of proximal section 802 when deployed during a medical procedure.

At both a proximal end and a distal end of proximal section 802, outer sheath 810a may be heat-fused or adhesive-bound to middle shaft 808a. Thus, tendon sheath 814 is immobilized within the proximal end and the distal end of section 802, while simultaneously free-floating within gap 812. Examples of adhesive material which may be used include, but are not limited to, ultraviolet-cured adhesive, instant-cured cyanoacrylate, and heat-cured adhesive.

Figure 8B:
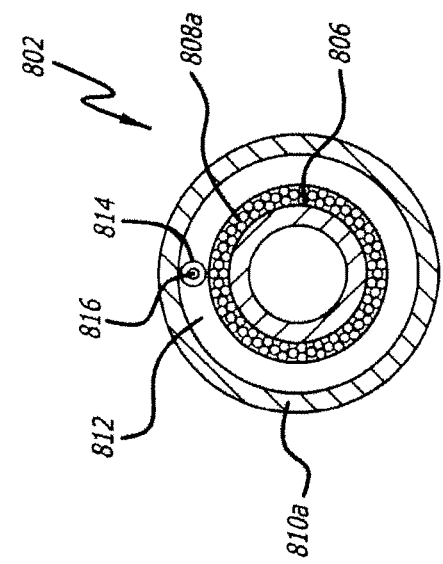
FIG. 8*b* is a cross-section of the catheter of FIG. 8*a* taken along lines B-B.

FIG. 8b represents a front cross-section view of catheter 800 taken at lines B-B of FIG. 8a. This cross-section is within the intermediate portion of proximal section 802 wherein gap 812 resides. In this view, catheter 800 includes inner shaft 806 which is surrounded by middle shaft 808a which in turn is surrounded by outer shaft 810a. In one embodiment, middle shaft 808a can include three coiled shafts (as described above) stacked closely together. Between middle shaft 808a and outer shaft 810a resides gap 812. As shown, tendon sheath 814 housing tendon 816 resides in gap 812. Tendon 816 can be used to control the movement of distal section 804 when catheter 800 is deployed within, for example, a curved anatomical path. The stacked coil configuration of middle shaft 808a should not allow longitudinal length changes in proximal section 802 even when a compression force is applied due to pulling of tendon 816 when deployed during a medical procedure.

Figure 8C:
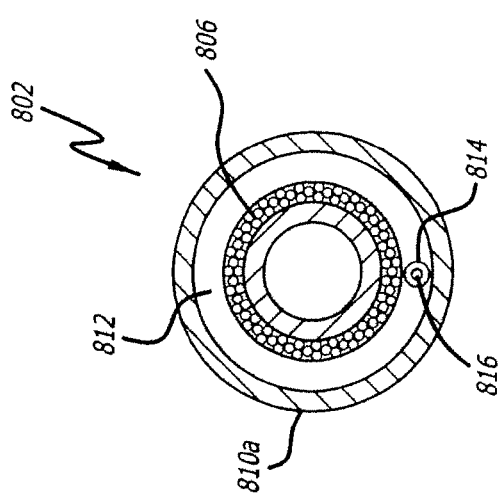
FIG. 8*c* is a cross-section of the catheter of FIG. 8*a* taken along lines C-C.

Similarly, FIG. 8c represents a front cross-section view of catheter 800 taken at lines C-C of FIG. 8a. As with FIG. 8b, this cross-section is also within the intermediate portion of proximal section 802 wherein gap 812 resides. In FIG. 8c, tendon sheath 816 is shown positioned at approximately 180° relative to tendon sheath 816 shown in FIG. 8b. Together, FIGS. 8b and 8c illustrate an embodiment of tendon sheath 816 half wrapped half way around middle shaft 808a within gap 812 of an intermediate portion of proximal section 802, e.g., FIGS. 8b and 8c show catheter 800 at two points between which tendon sheath 816 wraps one-half of a revolution around middle shaft 808a.

Referring to distal section 804 in FIG. 8a, catheter 800 can include middle shaft 808b housing inner shaft 806. That is, the luminal surface of middle shaft 808a can be completely or substantially in contact with the abluminal surface of inner shaft 806. In some embodiments, middle shaft 808b of distal section 804 should be more flexible relative to middle shaft 808a of proximal section 802. In some embodiments, middle shaft 808b is a coiled shaft and inner shaft 806 is fitted therein. In one embodiment, middle shaft 808b is made of a single coiled shaft. The single coiled shaft can be wound on a mandrel such that there are gaps in between adjacent coils forming a coiled tubular structure. In other words, less tension is applied to a wire as it is being wound around the mandrel than would be applied to a wire in which no gaps are desired. The result is a coiled tubular structure which is less rigid and allows for ease of deflection of distal section 804 when deployed during a medical procedure. Within distal section 804, tendon sheath 814 housing tendon 816 does not wrap around the mid shaft 808b but runs straight parallel to the longitudinal direction of the mid shaft, still captured with the mid shaft 808b and the outer shaft 810b. The catheter deflects towards the radial direction of the location of the tendon sheath 814. If only one tendon is used, the catheter only deflects in one direction.

As discussed previously, outer shaft 810b can serve as an outer housing for distal section 804. In some embodiments, tendon sheath 814 housing tendon 816 can reside between middle shaft 808b and outer shaft 810b of distal section 804. In one embodiment, tendon sheath 816 can be fixed in a longitudinal position between middle shaft 808b and outer shaft 810b. In some embodiments, tendon sheath 816 can be fixed by fusing the outer shaft 810b to the mid shaft 808b by heat. A tip anchor assembly 818 can be located at a distal end of distal section 804. Tip anchor assembly 818 can be made of a metal such as stainless steel or a polymer such as Pebax®, polyimide, or PEEK. In one embodiment, tip anchor assembly 818 can be a soft polymer that is mounted at the distal end of distal section 804 to reduce trauma incurred as catheter 800 moves through the body. In some embodiments, distal ends of outer shaft 810b, inner shaft 806 and tendon wire 816 can be fixed to tip anchor assembly 818.

Figure 8D:
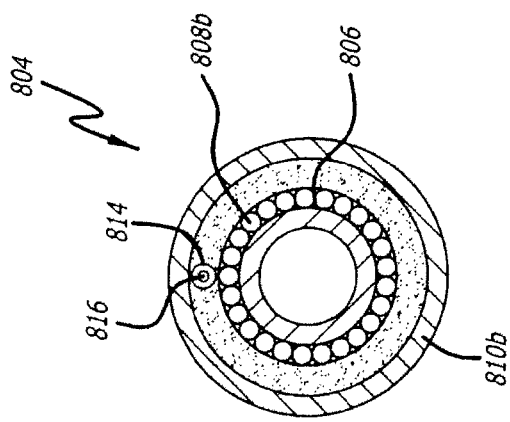
FIG. 8*d* is a cross-section of the catheter of FIG. 8*a* taken along lines D-D.

FIG. 8d represents a front cross-section view of catheter 800 taken at lines D-D of FIG. 8a. This cross-section is within distal section 804. In this view, catheter 800 includes inner shaft 806 which is surrounded by middle shaft 808b which in turn is surrounded by outer shaft 810b. In one embodiment, middle shaft 808b can include a single coiled shaft (as described above) for ease of flexibility. Tendon 816 can be used to control the movement of distal section 804 when catheter 800 is deployed within, for example, a curved anatomical path. The flexible nature of distal section 804 allows for deflection when a pull force is applied to a proximal end of tendon 816.

In one embodiment, catheter 800 includes a proximal hub (not shown) with an injection port. The injection port is connected to a needle lumen to allow fluid communication from the injection port to the needle lumen, thereby allowing the introduction of a bioagent from the injection port and into the needle lumen and then into the tissue penetrated by the distal tip of the needle. The proximal hub with the injection port may include a luer lock. In another embodiment catheter 800 may also include a self-seal valve and a flush port. The medical instrument, such as the needle, runs inside of the self-seal valve.

Figure 8E:
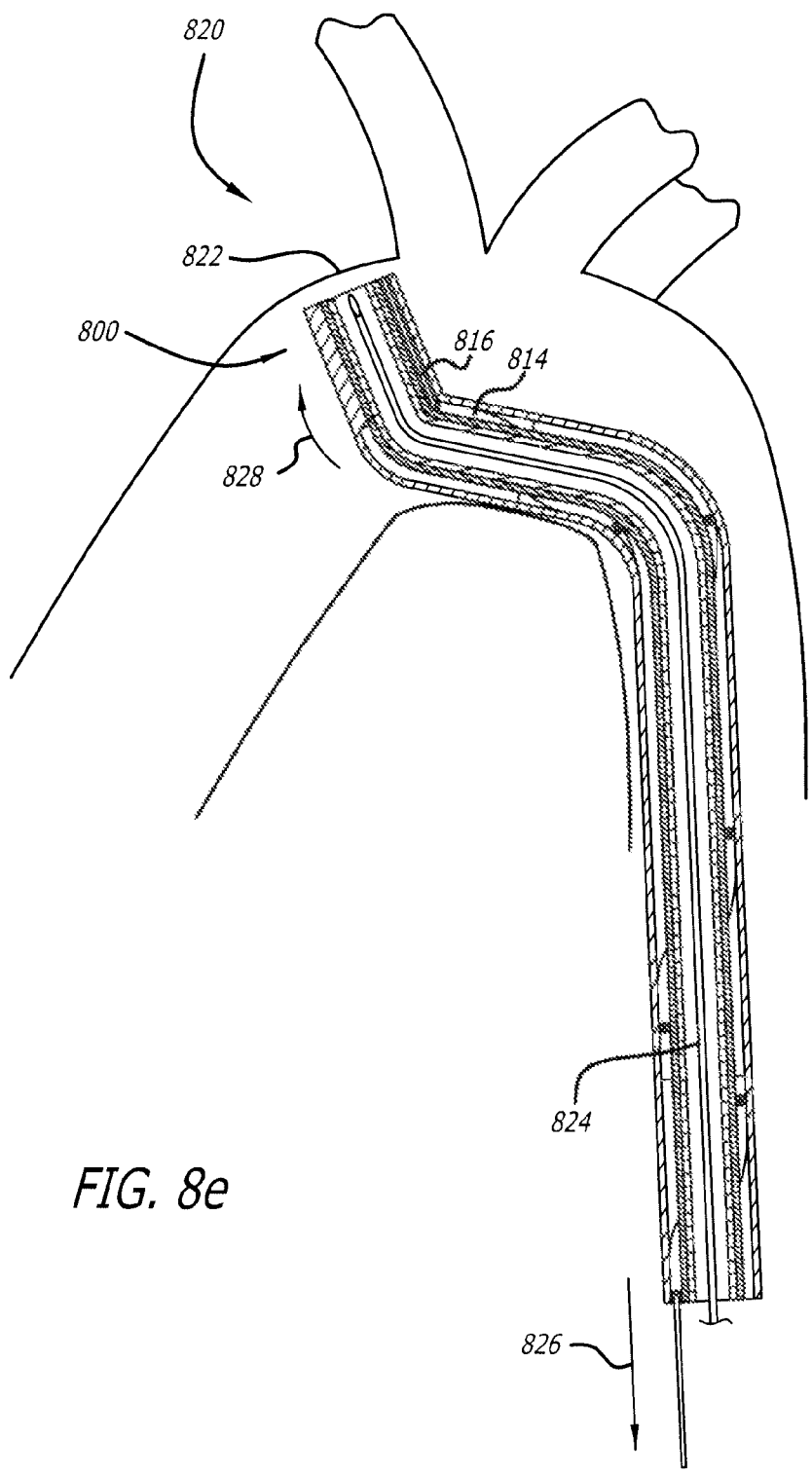
FIG. 8*e* illustrates the catheter of FIG. 8*a* being deployed in the aortic arch leading to the heart.

According to embodiments of the present invention, the construction and materials of catheter 800 allow for a controlled turning response of distal section 804 when a turning force is applied to proximal section 802 as illustrated in FIG. 8e. FIG. 8e illustrates a cross-section of catheter 800 disposed within aortic arch 820. Aortic arch 820 has a curved anatomical configuration. When a pull force is applied to tendon 816 (represented by arrow 826), distal section 804 deflects (represented by arrow 828) toward treatment site 822 even though a preferred orientation of distal section 804 is naturally oriented 180 degrees from the illustrated position. The natural orientation is due to the laws of physics which dictate that distal section 804 would naturally orient along the natural curvature of aortic arch 820 absent the embodiments described of the present invention. The angle of deflection may be between about 75 degrees and about 150 degrees. Once positioned at treatment site 822, a medical instrument such as a needle or a biopsy clamp 824 within a lumen of catheter 800 can be used to treat treatment site 822.

A deflectable catheter assembly has been described. Although the present invention has been described with reference to specific exemplary embodiments, it will be evident that various modifications and changes may be made to these embodiments without departing from the broader spirit and scope of the invention. For example, certain embodiments in which the first, second and third catheters are not coaxial are also within the scope of the present invention. Accordingly, the specification and drawings are to be regarded in an illustrative rather than a restrictive sense.

What is claimed is:
1. A catheter assembly comprising:
 a first catheter comprising a shaft having a proximal end and a distal end;
 a second catheter fitting coaxially within the first catheter and comprising a shaft having a proximal end and a distal end, the first catheter having at least one stiff portion and a deflectable portion distal to the stiff portion to allow deflection of the catheter from a first position to a second position,
wherein the at least one stiff portion comprises:
a liner;
a reinforcement material wrapped around an outer surface of the liner; and
a jacket wrapped around the reinforcement material; and
wherein the deflectable portion comprises the liner and the jacket and the reinforcement material does not extend into the deflectable portion;
a third catheter having a sheath and a medical instrument positioned within the sheath, the third catheter fitting coaxially within the second catheter; and
a stabilizer coupled to a distal end of said third catheter.

2. The catheter of claim 1 wherein the deflectable portion further comprises a second reinforcement material wrapped around the liner and attached between the liner and the jacket.

3. The catheter of claim 1 further comprising a soft tip portion attached to the distal end of the first catheter.

4. The catheter of claim 3 wherein the soft tip portion is a soft polymer ring.

5. The catheter assembly of claim 1 wherein the second catheter further comprises a shaft including at least one stiff portion and a deflectable portion.

6. The catheter of claim 5 wherein the deflectable portion comprises the liner and the jacket wherein the reinforcement material does not extend into the deflectable portion.

7. The catheter of claim 6 wherein the deflectable portion further comprises a second reinforcement material wrapped around the liner and attached between the liner and the jacket.

8. The catheter of claim 5 further comprising a soft tip portion attached to the distal end of the first catheter.

9. The catheter of claim 8 wherein the soft tip portion is a soft polymer ring.

10. The catheter assembly of claim 1 wherein the medical instrument comprises a needle.

11. The catheter assembly of claim 1 wherein the medical instrument comprises an optical fiber.

12. The catheter assembly of claim 1 wherein the medical instrument comprises an electrode.

13. The catheter assembly of claim 1 wherein the medical instrument comprises a sensor.

14. A catheter assembly comprising:
a first catheter having a first sheath and a first lumen;
a second catheter having a second sheath and a second lumen, the second catheter being coaxially disposed within the first lumen, wherein the first catheter has a preshaped portion and the second catheter comprising a shaft having a stiff portion and a deflectable portion,
wherein the stiff portion comprises:
a liner;
a reinforcement material wrapped around an outer surface of the liner; and
a jacket wrapped around the reinforcement material; and
wherein the deflectable portion comprises the liner and the jacket and wherein the reinforcement material does not extend into the deflectable portion; and
a third catheter having a third sheath which is coaxially disposed within the second lumen.

15. The catheter claim assembly of claim 14 wherein the deflectable portion allows a deflection from a first angle to a second angle and wherein the preshaped portion is substantially fixed in one angle.

16. The catheter claim assembly of claim 14 wherein the first catheter which has a preshaped portion is also deflectable from a preshaped position.

17. The catheter claim assembly of claim 14 further comprising a stabilizer coupled near a distal portion of the third catheter.

18. The catheter claim assembly of claim 14 wherein the third catheter comprises a helical shaped needle.

19. The catheter claim assembly of claim 14, wherein the deflectable portion is distal to the stiff portion.

20. The catheter claim assembly of claim 14 wherein the second catheter is slidably and rotatably mounted within the first lumen and wherein the third catheter is slidably and rotatably mounted within the second lumen.

21. A catheter assembly comprising:
a first catheter having a first sheath and a first lumen;
a second catheter having a second sheath and a second lumen, the second catheter being coaxially disposed within the first lumen, wherein at least one of the first catheter and the second catheter has a stiff portion comprising a reinforcing material and a jacket on the reinforcing material and a separate deflectable portion distal to the stiff portion configured to allow a deflection from a first angle to a second angle, wherein the reinforcing material does not extend into the deflectable portion such that the deflectable portion comprises the jacket on a liner;
a third catheter having a third sheath which is coaxially disposed within the second lumen.

22. The catheter claim assembly of claim 21 further comprising:
a stabilizer coupled near a distal portion of the third catheter.

23. The catheter claim assembly of claim 21, the third catheter further comprising a needle coaxially disposed within the third sheath.

24. The catheter claim assembly of claim 23 wherein the needle is a helical shaped needle.

* * * * *